United States Patent [19]

Boese

[11] Patent Number: 4,566,283

[45] Date of Patent: Jan. 28, 1986

[54] LOW TEMPERATURE DEVICE FOR COOLING SMALL SAMPLES

[75] Inventor: Roland Boese, Essen, Fed. Rep. of Germany

[73] Assignee: Nicolet Instrument Corporation, Madison, Wis.

[21] Appl. No.: 646,561

[22] Filed: Aug. 30, 1984

[51] Int. Cl.[4] .............................................. F17C 13/02
[52] U.S. Cl. .......................................... 62/49; 62/50; 62/514 R
[58] Field of Search ................. 62/45, 49, 50.1, 514 R

[56] References Cited

U.S. PATENT DOCUMENTS

| | | | |
|---|---|---|---|
| 3,163,013 | 12/1964 | Webster | 62/49 |
| 3,215,140 | 11/1965 | Caparrelli | 62/50 |
| 3,245,248 | 4/1966 | Ritter | 62/50 |
| 3,271,966 | 9/1966 | Webb | 62/45 |
| 3,648,018 | 3/1972 | Cheng et al. | 62/50 |

Primary Examiner—Ronald C. Capossela
Attorney, Agent, or Firm—Kinney & Lange

[57] ABSTRACT

Protected shall be an arrangement in which a liquid gas is evaporated within an insulated vessel below a hood, and in which the gas flows through a tube, which is within the hood, and penetrates through the bottom of the insulated vessel.

4 Claims, 1 Drawing Figure

LOW TEMPERATURE DEVICE FOR COOLING SMALL SAMPLES

BACKGROUND OF THE INVENTION

1. Field of the Invention

The invention refers to a low temperature device for the cooling of small samples. It can be used in the application of different spectroscopic methods, especially at X-ray and neutron diffraction, and for the investigation of different phases as well as electrical properties.

At such spectroscopic methods the temperature motion of atoms shall be reduced by cooling, temperature dependent phases shall be investigated, respectively. For this constant temperatures are necessary for longer periods.

2. Description of the Prior Art

It is known that measurements on small samples are performed at low temperatures by passing a temperature controlled gas stream over a sample. The producing of the cold gas stream is either done by evaporation of e.g. liquid nitrogen with following temperature control (System FR 524, Enraf Nonius, Delft, Enraf Nonius bulletin (1964) or by cooling gaseous nitrogen in a heat exchanger (System Lt-1, Nicolet/Fremont, California (1979)). At both systems a distance of approximately 80–150 cm is to be bridged by insulated tubes from the coldest point of the gaseous stream to the sample.

In order to achieve the lowest possible temperature at the sample there must be a high stream speed because of the long distances at which the gas, according to experience, warms up. This causes a high consumption of liquid gas. Even at high stream speeds temperatures only above 100 K. can be achieved with liquid nitrogen in the surrounding of the sample. In addition long distances reduce temperature stability at the sample's position if the surrounding temperature differs.

SUMMARY OF THE INVENTION

The invention basically intends to cool small samples with high stability of temperature down to the lowest temperature which can be achieved with a minimum consumption of liquid gas.

In order to achieve a short distance from the position of the gas at its boiling point to the position of the sample the following arrangement can be used: a liquid gas is evaporated, and the gas is passed through a tube being inside an insulated hood. The tube is surrounded by liquid gas and penetrates directly through the bottom of an outer insulated vessel. With this the gas keeps the low temperature of its phase transition up to the point of the penetration through the vessel. Within the tube there can be a heating which allows a fine control of the gas stream's temperature. Directly at the tube or with connections in between there is fixed the nozzle for blowing at the sample.

This arrangement achieves because of these short distances a low consumption of liquid gas, a low final temperature, a high stability of temperature; any temperature above the boiling point can be controlled. If a recycling of the gas is wanted because of its high costs, it can be done if the sample is enclosed by a chamber and the evaporation vessel is closed. In this case, the chamber and the insulated vessel must be connected by a tube with a gas collector.

The inner hood can be a glass Dewar or can consist of any other insulating materials.

BRIEF DESCRIPTION OF THE DRAWINGS

One application of the inventionship is shown in the drawing, and it's described in the following:

DETAILED DESCRIPTION OF THE PREFERRED EMBODIMENTS

Figure 1:
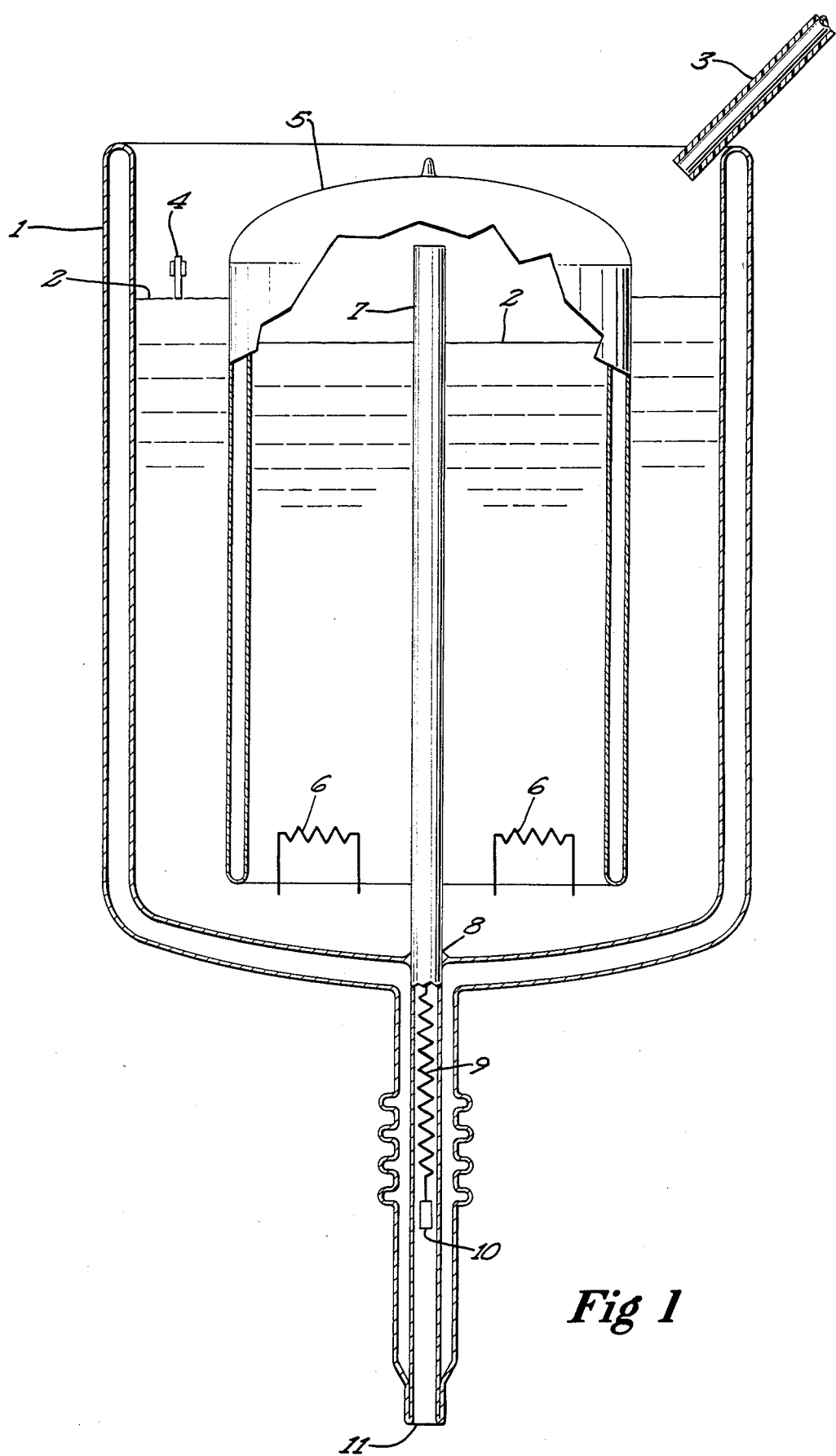

Within a vacuum insulated and silver coated insulation vessel (1) there is liquid nitrogen (2) which is refilled by an insulated tube (3), controlled by a level sensor (4). Below a just so insulated hood (5) nitrogen is evaporated by an electric resistance heating (6) and flows through a tube (7) which penetrates through the bottom of the vessel (1). At the penetration point (8) the nitrogen has got the temperature of its boiling point and can be temperature controlled below the penetration point with a heating (9) and a thermo couple (10). Below the outlet (11) a connection tube and a nozzle or a nozzle directly can be fixed for blowing towards the sample.

I claim:

1. A device for providing a low temperature gas stream for cooling small samples undergoing spectroscopic analysis comprising:
    insulated outer container means for containing liquified gas;
    hood means within the outer container means for trapping evaporated liquified gas;
    means within said hood means for evaporating liquified gas therein; and
    tube means extending from the evaporated liquified gas trapped within said hood means through said outer container means.

2. The low temperature device of claim 1 further comprising means for controlling the temperature of evaporated liquified gas flowing from said outer container through said tube means.

3. The low temperature device of claim 2 further comprising:
    means for sensing the level of liquified gas within said outer container; and
    means for refilling said outer container.

4. The low temperature device of claim 1 further comprising:
    means for sensing the level of liquified gas within said outer container; and
    means for refilling said outer container.

* * * * *